(12) United States Patent
Pizzoni et al.

(10) Patent No.: US 11,116,786 B2
(45) Date of Patent: Sep. 14, 2021

(54) COMBINATION OF GLYCOSAMINOGLYCANS AND AN ANTACID AGENT AND COMPOSITIONS THEREOF

(71) Applicant: APHARM S.R.L., Arona NO (IT)

(72) Inventors: Angelo Pizzoni, Arona NO (IT); Paolo Pizzoni, Arona NO (IT)

(73) Assignee: APHARM S.R.L., Arona NO (IT)

( * ) Notice: Subject to any disclaimer, the term of this patent is extended or adjusted under 35 U.S.C. 154(b) by 25 days.

(21) Appl. No.: 15/762,602

(22) PCT Filed: Sep. 30, 2016

(86) PCT No.: PCT/IB2016/001423
§ 371 (c)(1),
(2) Date: Mar. 23, 2018

(87) PCT Pub. No.: WO2017/055909
PCT Pub. Date: Apr. 6, 2017

(65) Prior Publication Data
US 2018/0280426 A1    Oct. 4, 2018

(30) Foreign Application Priority Data

Oct. 1, 2015 (IT) .......................... UB2015A004158
Apr. 26, 2016 (IT) .......................... UA2016A002869

(51) Int. Cl.
| | | |
|---|---|---|
| *A01N 43/04* | (2006.01) |
| *A61K 31/70* | (2006.01) |
| *A61K 31/726* | (2006.01) |
| *A61K 33/06* | (2006.01) |
| *A61K 47/36* | (2006.01) |
| *A61K 45/06* | (2006.01) |
| *A61K 9/10* | (2006.01) |
| *A61K 9/08* | (2006.01) |
| *A61K 31/737* | (2006.01) |
| *A61K 31/728* | (2006.01) |
| *A61K 9/00* | (2006.01) |
| *A61K 47/26* | (2006.01) |
| *A61K 47/32* | (2006.01) |
| *A61K 47/34* | (2017.01) |

(52) U.S. Cl.
CPC .......... *A61K 31/726* (2013.01); *A61K 9/0095* (2013.01); *A61K 9/08* (2013.01); *A61K 9/10* (2013.01); *A61K 31/728* (2013.01); *A61K 31/737* (2013.01); *A61K 33/06* (2013.01); *A61K 45/06* (2013.01); *A61K 47/26* (2013.01); *A61K 47/32* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 4,676,984 A | * | 6/1987 | Wu ....................... | A61K 9/0095 424/689 |
| 6,589,507 B1 | * | 7/2003 | Bauer .................. | A61K 9/0007 424/44 |
| 9,241,953 B2 | * | 1/2016 | Pizzoni ................ | A61K 31/728 |
| 2012/0107064 A1 | | 5/2012 | Chen | |
| 2014/0107064 A1 | | 4/2014 | Pizzoni | |

FOREIGN PATENT DOCUMENTS

| | | |
|---|---|---|
| EP | 1304338 | 4/2003 |
| WO | 2010136872 | 12/2010 |

OTHER PUBLICATIONS

Patel et al. Indian J. Physiol Pharmacol (2000), vol. 44, pp. 350-351.*
Patel et al. Indian J. Physiol. Pharmacol. (2002), vol. 44, pp. 350-354.*
Zatz et al. Journal of Pharmaceutical Sciences (1984), vol. 73, pp. 468-471.*
Wiet et al. Journal of Food Science (1992), vol. 57, pp. 1014-1019.*
Sanchez et al. Pharmacology & Pharmacy (2014), vol. 5, pp. 216-223.*
International Search Report and Written Opinion dated Feb. 10, 2017 for PCT/IB2016/001423.
European Search Report and written opinion dated May 31, 2016 for Italian priority application No. 102015000057332.
IPRP dated Apr. 3, 2018 for PCT/IB2016/001423.

* cited by examiner

*Primary Examiner* — Patrick T Lewis

(57) ABSTRACT

The present invention refers to a combination of hyaluronic acid, chondroitin sulfate in combination with at least one antacid agent, in particular magaldrate, for the prevention or treatment of gastric hyperacidity and gastroesophageal reflux and related pathologies thereof. More particularly, the combination is used for the preparation of oral compositions with at least one pharmaceutical carrier and advantageously that comprise a bioadhesive agent as well.

11 Claims, No Drawings

COMBINATION OF GLYCOSAMINOGLYCANS AND AN ANTACID AGENT AND COMPOSITIONS THEREOF

RELATED APPLICATIONS

This application is a US national phase application of International application number PCT/IB2016/001423, filed 30 Sep. 2016, which designates the US and claims priority to Italian application UB2015A004158 filed 1 Oct. 2015 and Italian application UA2016A002869 filed 26 Apr. 2016, the contents of each of which are hereby incorporated by reference as if set forth in their entireties.

SUMMARY OF THE INVENTION

The present invention refers to a combination of hyaluronic acid, chondroitin sulfate and at least one antacid agent, in particular magaldrate, for the prevention or treatment of gastric hyperacidity and gastroesophageal reflux and related pathologies thereof. More particularly, the combination is used for the preparation of oral compositions with at least one pharmaceutical carrier and that advantageously comprise a bioadhesive agent as well.

TECHNICAL FIELD

Gastric hyperacidity (or heartburn or pyrosis) is a very common symptom and it is so frequent that nearly all the adult population suffers from it. The increase of the acidity can be connected to several factors. It can represent an occasional symptom, connected to too big meals, food difficult to be digested, stress, drugs or alcohol and cigarette smoke excess. On the other hand, it can as well represent a constant problem, in case of presence of a chronic gastritis or, even worse, an ulcer.

Glycosaminoglycans are a polysaccharide family formed by the repetition of an uronic acid, glucuronic or iduronic acid, 1→4 or β 1→3 bonded to a hexosamine, glucosamine or galactosamine residue. Hexosamine and uronic acid residues can be sulfated in various ways. In the glycosaminoglycan family, in addition to heparin sulfate and heparan sulfate, hyaluronic acid and chondroitin sulfate are also included. Physiologically, glycosaminoglycans are organized in proteoglycans formed by a protein nucleus to which the glycosaminoglycan is bonded by means of a connecting region. These structures have a control role in biochemical reactions by means of the captation and release of proteins and growth factors.

In particular, chondroitin sulfate is localized in the cartilages and in the epithelial portion of the gastric mucosa or in the urothelium. To the cartilages it confers the peculiar elasticity and controls their resistance, while in the mucosa and in the epithelium it protects the epithelium itself from the acid attack in case of gastric epithelium and from potassium in case of urothelium. In diseases where the amount of chondroitin sulfate is low such as e.g. in gastritis or interstitial cystitis, the administration of chondroitin sulfate helps to alleviate the inflammation and correlated damages due to the low chondroitin sulfate content. Extracted chondroitin sulfate has usually an average molecular weight between 10,000 and 50,000 Da. Biosynthetic chondroitin sulfate can be obtained starting from the K4 polysaccharide, e.g., according to the method described in EP 1304338. Its average molecular weight is between 12,000 and 15,000 Da, even though it is possible to prepare products having lower or higher molecular weight.

Hyaluronic acid is usually found as a regular non-sulfated macromolecule formed by a disaccharide linear sequence of glucuronic acid 1-3 bonded to N-acetylglucosamine, while chondroitin sulfate is mainly present in two distinct forms: the chondroitin-4-sulfate (or ChSA) and the chondroitin-6-sulfate (or ChSC). Chondroitin sulfate is formed by the disaccharidic repetition containing β 1→3 glucuronic acid bonded to galactosamine which is sulfated either in position 4 or in position 6. In the same molecule there are both ChSA and ChSC groups. Occasionally there can be small amounts of disulfated and non-sulfated disaccharides in the polysaccharide chain. Proteoglycans containing chondroitin sulfate are made of a hyaluronic acid backbone on which protein chains are attached (protein core) bringing the arms of the chondroitin sulfate chains. As a consequence a macromolecule with very high viscosity is formed, the viscosity being due to the very high molecular mass and also to the structural features of its components.

Extracted hyaluronic acid has average molecular weight in the order of $10^5$-$10^6$ Da. Many so-called "antacid" drugs are known, which act on the gastric hyperacidity and on the gastroesophageal reflux, either directly, i.e. by buffering the pH of the gastric mucosa, or indirectly, e.g. by inhibiting the acid secretion from the stomach.

Magaldrate is the International Nonproprietary Name of magnesium aluminate monohydrate, and is usually used as an antacid drug for the treatment of duodenal ulcer, gastric ulcer and reflux esophagitis.

OBJECTS OF THE INVENTION

It is an object of the invention to provide a combination of active ingredients useful for the treatment of gastric hyperacidity and/or gastroesophageal reflux and related pathologies thereof, that is well tolerated and provides at the same time cytoprotective action.

It is another object of the invention to provide pharmaceutical compositions comprising said combination and the use thereof in therapy.

It is a further object of the invention to provide a combination of active ingredients useful for the treatment of gastric hyperacidity and gastroesophageal reflux and related pathologies thereof, that allows to administer an antacid dose lower than the usually employed doses.

DESCRIPTION OF THE INVENTION

It has been found that a combination of hyaluronic acid, chondroitin sulfate and an antacid, preferably magaldrate, can be useful in therapy, in particular for the preparation of pharmaceutical compositions intended for the treatment of gastric hyperacidity and gastroesophageal reflux (or gastric reflux) and related pathologies thereof.

Therefore, according to one of the aspects, a subject-matter of the invention is a combination of hyaluronic acid or a pharmaceutically acceptable salt thereof, chondroitin sulfate or a pharmaceutically acceptable salt thereof, and at least one antacid agent.

"Antacid" or "antacid agent" means herein a compound that can relieve the heartburn feeling (or pyrosis) typical of acid hypersecretion.

Therefore according to the present invention, the phrases "antacid" or "antacid agent" are intended to encompass the agents reducing the above reported symptoms both directly, thanks to a neutralizing effect of the gastric acidity, and indirectly by means of the inhibition of the acid secretion at gastric level.

Among the antacid agents acting directly, according to the invention magaldrate, sucralfate; citrates, e.g. sodium or potassium; magnesium oxide; magnesium hydroxide; magnesium carbonate; magnesium silicates, e.g. magnesium trisilicate; basic aluminum aminoacetate; hydrated aluminum oxide; aluminum hydroxides; bicarbonates, e.g. sodium bicarbonate; carbonates, e.g. calcium carbonate; alginic acid; sodium alginate; calcium phosphate, hydrotalcite; aluminum glycinate; galactan sulfate; myrtecaine, e.g. myrtecaine lauryl sulfate; palygorskite; and mixtures thereof, are preferred.

Antacid agents acting indirectly comprise for example proton pump inhibitors and H2-receptor antagonists.

Some preferred proton pump inhibitors according to the invention are for example pantoprazole, esomeprazole, lansoprazole, esomeprazole, omeprazole, rabeprazole, ilaprazole, tenatoprazole, dexlansoprazole, rabeprazole and the pharmaceutically acceptable salts thereof.

Some preferred H2-receptor antagonists according to the invention are for example ranitidine hydrochloride, cimetidine, famotidine, nizatidine, roxatidine and the pharmaceutically acceptable salts thereof.

More antacid agents can be combined together according to the present invention.

For a particularly preferred embodiment, the antacid agent is magaldrate, alone or in combination with other antacid agents, preferably alone.

Hyaluronic acid and chondroitin sulfate of the present formulation are preferably used as their alkaline salts, such as for example sodium salt or potassium salt, the sodium salt being preferred.

Unless otherwise specified, the reported doses for the hyaluronic acid and chondroitin sulfate hereinafter are therefore referred to sodium hyaluronate and sodium chondroitin sulfate.

Preferably the combination of the invention is a fixed combination of sodium hyaluronate/sodium chondroitin sulfate/antacid. The relative amounts of the active ingredients in the combination can vary. For example, with respect to the weight amount of sodium hyaluronate it is possible to use from 1.5 to 5 weight times of chondroitin sulfate, for example about 2-3 weight times and from 3 to 20 weight times of magaldrate, for example from 5 to 15 weight times.

Preferred combinations consist of sodium hyaluronate/sodium chondroitin sulfate/magaldrate combinations with a reciprocal weight ratio of about 1/2.5/12-13. However other weight ratios can be used and fall within the scope of protection of the present invention.

For the antacid not acting directly but providing an inhibitory action of acid secretion, the dose will be selected from the person skilled in the field on the basis of the doses usually employed in the therapy for the specific molecule.

According to another of the aspects thereof, a subject-matter of the invention are pharmaceutical compositions which comprise the combination as defined above and their use in therapy, particularly for the treatment of gastric hyperacidity and gastroesophageal reflux and related pathologies thereof.

For the intended use, the combination of the invention is formulated with the commonly used pharmaceutical carriers for the preparation of compositions for the oral administration.

Hyaluronic acid, advantageously in the form of sodium salt, has preferably an average molecular weight not lower than $10^5$ Da.

Chondroitin sulfate has advantageously average molecular weight of 5,000 to 50,000, advantageously 10,000 to 50,000, preferably 12,000 to 30,000.

The compositions of the invention are preferably in suitable oral unit doses, such as for example solid unit doses, such as tablets, powders, or granulates in sachets, stick packs, or in liquid unit doses such as oral solutions or suspensions. Said unit forms contain preferably 30 mg to 200 mg of hyaluronic acid or a pharmaceutically acceptable salt thereof, 50 mg to 500 mg of chondroitin sulfate or a pharmaceutically acceptable salt thereof and 300 to 1000 mg of magaldrate.

According to a preferred embodiment, the compositions of the invention comprise 30 to 100 mg of sodium hyaluronate, 80 to 200 mg of sodium chondroitin sulfate and 400 to 600 mg of magaldrate.

Preferred compositions comprise about 40 mg of sodium hyaluronate, about 100 mg of sodium chondroitin sulfate and about 500 mg of magaldrate.

For the preparation of the pharmaceutical compositions according to the invention, the magaldrate can be used in solid form or in the form of a suspension (or paste), advantageously it is used in the form of suspension, e.g. a 20% suspension. Such form is commercially available.

Carriers for the tables include for example starches, cellulose and derivatives thereof; lubricants such as for example talc, stearic acid or magnesium stearate; diluents such as for example talc, powdered cellulose, lactose, polyethylene glycol, starches such as for example corn or corn starch, mannitol, sorbitol; disaggregating agents such as for example microcrystalline cellulose or crospovidone; binders such as for example methylcellulose, sodium carboxymethyl cellulose; sweeteners, such as for example sucrose, dextrose, mannitol, saccharin; or flavoring agents such as for example natural or synthetic oils.

Carriers for disintegrable tablets for oral use (to be chewed) include for example lubricant agents, binders, sweeteners, flavoring agents, bioadhesives or disaggregating agents.

Carriers for liquid suspensions or solutions, usually aqueous, include for example antioxidants, such as for example sodium metabisulfite or sodium sulfite, thickening agents, such as for example microcrystalline cellulose, hydroxypropyl cellulose, carboxymethyl cellulose or polyvinylpyrrolidone, gums, such as xanthan gum, preservatives such as for example methyl paraben, ethyl paraben, sodium ethylendiaminetetracetate, sodium benzoate or an alkaline salt of ascorbic acid, as well as flavoring agents and sweeteners.

Sweeteners contained in the chewable tablets for oral use and in the liquid suspensions or solutions can be natural sugars, optionally reduced, such as for example sucrose, dextrose, xylitol, mannitol or sorbitol, or a synthetic product such as for example sodium saccharin or aspartame. Acidifying agents can also be added. Flavoring agents are pharmaceutically acceptable flavors and tastes from synthetic oils or natural oils, the latter extracted from plants, flowers, fruits and combinations thereof, such as for example cinnamon, mint, anise, and citrus fruits leaves, bitter almonds, citrus fruits, in particular orange and/or lemon, lime and grapefruit oils. Caramel, milk, chocolate, vanilla or eucalyptus flavors and fruit essences, in particular apple, pear, peach, strawberry, apricot, orange, lemon and grapes can be also advantageously used.

The compositions of the present invention are formulated in an oral composition, advantageously liquid, wherein the active ingredients are mixed with a bioadhesive agent which can adhere to the esophagus wall together with the combination of active ingredients of the invention, therefore protecting or healing the damaged epithelium.

Therefore, according to a preferred embodiment, the compositions of the invention comprise hyaluronic acid, chondroitin sulfate (both preferably in the form of sodium salt) and at least one antacid, preferably magaldrate, together with a pharmaceutical carrier comprising at least one water-soluble bioadhesive agent. The use of the bioadhesive agent provides new oral liquid compositions with a viscosity particularly suited to the therapeutic use of the invention.

The combination and the compositions of the invention are advantageously protein-free, where the phrase "protein-free" means that the active ingredients contained here are purified products containing less than 1% of protein. In this way, the risk of allergy onset in the subjects to whom said combination or compositions are administered is drastically reduced.

The bioadhesive molecules are substances well-known for their ability to allow the adhesion of the active ingredients to the action sites for the local administration of drugs or for the coating of some parts of the body.

The preferred liquid composition according to the invention will preferably have viscosity useful for the administration of the active ingredient by using a simple or single-dose container in a reproducible form immediately ready for the user. Preferably, the viscosity of the liquid composition will be comprised between 6,000 and 7,000 centipoise, with an average value of 6,500 centipoise (measured as suggested in the Experimental Section).

Therefore, according to this preferred embodiment, the present invention provides an aqueous liquid oral composition comprising the combination of the invention as defined above, particularly the combination defined as preferred according to the invention, and a bioadhesive which is advantageously present in a total concentration ranging from 0.5 to 4 wt % relative to the total weight of the composition, advantageously around 2.5-3%.

Since hyaluronic acid and chondroitin sulfate are themselves polymers with high viscosity properties and high bioadhesive activity, it is desirable to use polymers completely compatible with these active ingredients.

Said compatible bioadhesive polymers are selected for example from the group consisting of poloxamers, such as for example ethylene and propylene oxide copolymers, in particular poloxamer 407, vinylpyrrolidone polymers, such as for example polyvinylpyrrolidone Kw 24-32, corresponding to a molecular weight of 40,000, and cellulose derivatives such as for example hydroxypropyl cellulose.

Preferably, said water-soluble viscosity agents having high bioadhesive properties, such as for example the poloxamer 407, polyvinylpyrrolidone or hydroxypropyl cellulose, are mixed with hyaluronic acid having molecular weight between 100 and 3,000 Kdalton and chondroitin sulfate with a molecular weight between 5 and 40 Kdalton and magaldrate, to obtain a clear solution. Said solution can be easily used as liquid pharmaceutical form having very good antacid activity.

Together with the main components and the bioadhesive, the preferred compositions of the present invention can contain preservative agents in order to increase the stability of the composition as well as sweetening agents, flavoring agents and, optionally, coloring agents to increase and optimize the organoleptic features of the liquid oral preparation.

Preservatives, such as sodium benzoate, sorbic acid and salts thereof, particularly potassium sorbate, EDTA or salts thereof, and parabens such as methyl and ethyl paraben, can be present in a concentration ranging from 0.01 to 0.4 wt %.

Sweetening agents can be natural sugars, optionally reduced, such as for example sucrose, dextrose, xylitol, mannitol or sorbitol, or a synthetic product such as for example sodium saccharin or aspartame.

Flavoring agents will be selected from the person skilled in the field based on the organoleptic properties of the composition. Flavoring agents can be selected from the group consisting of pharmaceutically and nutritionally acceptable flavors and from tastes of synthetic oils or natural oils, the latter being extracted from plants, leaves, flowers, fruits and combinations thereof, such as for example cinnamon, mint, anise, and citrus fruit leaves, bitter almonds, citrus fruits, in particular orange and/or lemon, lime and grapefruit oils. Caramel, milk, chocolate, vanilla or eucalyptus flavors and fruit essences, in particular apple, pear, peach, strawberry, apricot, orange, lemon and grapes, can be also advantageously used. The preferred flavoring agents are those imparted by mint or fruits, such as for example grapes, cherry or citrus fruits, in particular orange and lemon, from flavors and mixtures thereof.

Advantageously, the preferred liquid oral compositions of glycosaminoglycans of the present invention are the aqueous mixtures preferably in the form of unit dose, each comprising:

(a) sodium hyaluronate in an amount of 30 to 100 mg;
(b) sodium chondroitin sulfate in an amount of 80 to 200 mg;
(c) magaldrate in an amount of 400 to 600 mg; and
(d) at least one bioadhesive polymer in a total amount of 100 to 400 mg, together with conventional carriers and excipients, said dose unit being on the whole about 10 ml.

The liquid compositions of the invention have pH advantageously comprised between 7.8 and 8.4.

Particularly preferred compositions are reported in the following experimental section. A particularly preferred composition is the composition of Example 1.

The unit doses can be sachets, small glass or plastic bottles or any other containers available in the current pharmaceutical technology, including multi-dose containers, even though the single-dose unit doses are preferred according to the invention, advantageously the stick pack sachets.

The compositions in the form of unit doses in sachets have to be directly taken.

The preferred liquid oral compositions of the present invention can be prepared according to the methods known in the pharmaceutical technology.

According to a further aspect, the invention provides a process for the preparation of a liquid oral composition, characterized in that purified water is charged in a suitable reactor and is heated to 60° C. Possible cellulosic polymers and gums are added under stirring and left under stirring until complete solubilization. Sodium hyaluronate and chondroitin sulfate are added while keeping the stirring. Antacid, preferably magaldrate, advantageously in the form of suspension as indicated above, and the bioadhesive agent followed by the desired preservatives and flavors, are added and the stirring is continued for few tens of minutes.

The preferred liquid oral compositions according to the present invention are useful for the easy administration of the combination of the invention, even at high doses in liquid form having suitable bioadhesive properties. In particular, they are compositions for the treatment or prevention of gastric hyperacidity and gastroesophageal reflux and related pathologies thereof, such as duodenal and gastric ulcer, reflux esophagitis, gastritis and gastroduodenitis.

The Applicant carried out tests on the composition of the following Example 1, which demonstrated that the combination of the invention, particularly the combination formulated with the bioadhesive agent as specified above, shown to be particularly effective in the treatment of hyperacidity and gastroesophageal reflux and related pathologies. In addition, the combination allowed to reduce in the unit doses the antacid dose with direct action with respect to the doses commonly used in therapy and/or to reduce the posology. For example, the combination allowed to reduce the magaldrate dose in the unit doses with respect to the doses commonly used in therapy, which consider about 800 mg for unit dose to be administered 4 times a day (for a total dose of 3.2 g daily); moreover, in the tests performed, the composition of Example 1 has been administered only twice a day (for a total dose of 1 g daily), with surprisingly better effects with respect to the actual therapy.

The presence of glycosaminoglycans, in particular hyaluronic acid, allowed to obtain a cytoprotective effect, by promoting the healing of the gastroesophageal mucosa cells damaged by the hyperacidity.

According to another of the aspects thereof, a subject-matter of the invention is a method for the treatment and prevention of hyperacidity and gastroesophageal reflux and related pathologies thereof, comprising the administration of the combination or compositions according to the invention to a subject in need thereof.

The following examples illustrate the invention. In said examples purified sodium hyaluronate, from extraction with average molecular weight of about $10^6$ Da and purified sodium chondroitin sulfate, from extraction with an average molecular weight of 30,000 Da, have been used.

Example 1

A liquid composition in single-dose sachets (stick pack) of 10 ml each is prepared

| Ingredients | mg/10 ml |
| --- | --- |
| sodium hyaluronate | 46.719 |
| sodium chondroitin sulfate | 116.798 |
| xylitol powder (xylisorb 300) | 1262.315 |
| poloxamer 407 | 303.000 |
| polyvinylpyrrolidone | 280.517 |
| sodium benzoate | 10.523 |
| potassium sorbate | 21.035 |
| flavor | 2.336 |
| magaldrate (20% suspension) | 2500.000 |
| sucralose | 1.685 |
| xanthan gum | 17.969 |
| water | 667.660 |

Example 2

A liquid composition in single-dose sachets of 10 ml each is prepared

| Ingredients | mg/10 ml |
| --- | --- |
| xanthan gum | 28 |
| hydroxypropyl-methyl cellulose | 165 |

-continued

| Ingredients | mg/10 ml |
| --- | --- |
| sodium hyaluronate | 41 |
| sodium chondroitin sulfate | 103 |
| xylitol C | 2473 |
| Poloxamer 407 | 297 |
| polyvinylpyrrolidone | 275 |
| magaldrate | 500 |
| paramethyl paraben | 11 |
| paraethyl paraben | 11 |
| flavor | q.s. |
| acidifier | q.s. |
| water | q.s. |

Example 3

A liquid composition in single-dose sachets of 10 ml each is prepared

| Ingredients | mg/10 ml |
| --- | --- |
| sodium hyaluronate | 68.926 |
| sodium chondroitin sulfate | 172.288 |
| xylitol powder (xylisorb 300) | 2481.132 |
| poloxamer 407 | 148.889 |
| polyvinylpyrrolidone | 275.683 |
| sodium benzoate | 10.342 |
| potassium sorbate | 20.672 |
| flavor | 2.296 |
| magaldrato | 529.671 |
| water | q.s. |

Example 4

A liquid composition in single-dose sachets of 10 ml each is prepared

| Ingredients | mg/10 ml |
| --- | --- |
| xanthan gum | 28 |
| hydroxypropyl-methyl cellulose | 165 |
| sodium hyaluronate | 41 |
| sodium chondroitin sulfate | 103 |
| xylitol C | 2473 |
| Poloxamer 407 | 297 |
| polyvinylpyrrolidone | 275 |
| sucralfate | 1,000 |
| paramethyl paraben | 11 |
| paraethyl paraben | 11 |
| flavor | q.s. |
| acidifier | q.s. |
| water | q.s. |

Example 5

A liquid composition in single-dose sachets of 10 ml each is prepared

| Ingredients | mg/10 ml |
| --- | --- |
| sodium hyaluronate | 68.926 |
| sodium chondroitin sulfate | 172.288 |
| xylitol powder (xylisorb 300) | 2481.132 |
| poloxamer 407 | 148.889 |
| polyvinylpyrrolidone | 275.683 |
| sodium benzoate | 10.342 |

-continued

| Ingredients | mg/10 ml |
|---|---|
| potassium sorbate | 20.672 |
| flavor | 2.296 |
| magnesium hydroxide and hydrated aluminum oxide | 600 |
| water | q.s. |

Example 6

Method for the Preparation of the Composition of Example 1

Charge purified water in a perfectly clean and sanitized suitable mixer. Switch on the heating by setting the temperature to 60° C. At 60° C., add under stirring hydroxypropyl-methyl cellulose and xanthan gum and leave under stirring until complete solubilization. Proceed by adding sodium hyaluronate and chondroitin sulfate. Keep under stirring and add poloxamer, polyvinylpyrrolidone and magaldrate. Add the xylitol and leave under stirring for other 40 minutes. Later, cool down and add the parabens and flavors, under stirring. Adjust the pH of the product with the acidifier and keep under stirring for at least 15 minutes.

Example 7

Measurement of the Viscosity of the Composition of Example 1

Sample Preparation

A sample (200 ml) is taken from the batch and is conditioned at a temperature of 25-26° C.

Instruments

Brookfield DV-II plus

Measurement with Brookfield DV-II Plus

The viscometer must be calibrated with the Quality Control standards.

1. Start the instrument by setting the switch placed on the back panel in the ON position and perform the autocalibration.

2. Pull down the viscometer in the measuring position.

3. Fix the viscometer by rotating in clockwise direction the suitable rotor to measure the viscosity according to the following scheme:

| | |
|---|---|
| RV1 | 500-1500 cPs |
| RV2 | 1500-5000 cPs |
| RV3 | 5000-15000 cPs |
| RV4 | 15000-25000 cPs |
| RV5 | 25000-50000 cPs |
| RV6 | 50000-150000 cPs |
| RV7 | 150000-500000 cPs |

Immerse the Rotor into the Sample.

4. Select the type of rotor on the display
5. Select the speed
6. Select the unit of measurement cP (centiPoise)
7. Press the "Motor ON/OFF" button, measure the viscosity at speed 4 and speed 10 and calculate the viscosity as the arithmetic mean of the obtained values in Cp (centiPoise).

The obtained viscosity values for the composition of Example 1, range from 6000 to 7000 centipoise, with an average value of 6500 centipoise.

The invention claimed is:

1. A liquid pharmaceutical composition consisting of
    hyaluronic acid or a pharmaceutically acceptable salt thereof,
    chondroitin sulfate or a pharmaceutically acceptable salt thereof,
    magaldrate,
    a bioadhesive agent, and
    at least one pharmaceutically acceptable carrier or excipient wherein said liquid pharmaceutical composition is in unit doses consisting of 30 to 100 mg of sodium hyaluronate and 80 to 200 mg of sodium chondroitin sulfate, 400 to 600 mg of magaldrate and 100 to 400 mg of bioadhesive agent.

2. The liquid pharmaceutical composition according to claim 1, in the form of unit doses, each consisting of:
    a. sodium hyaluronate in an amount of 35 to 45 mg;
    b. sodium chondroitin sulfate in an amount of 90 to 110 mg;
    c. magaldrate in an amount of 450 to 550 mg; and
    d. at least one bioadhesive polymer in a total amount of 250 to 350 mg.

3. The liquid pharmaceutical composition according to claim 1 wherein said bioadhesive polymer is selected from the group consisting of poloxamers, copolymers of ethylene and propylene oxide, vinylpyrrolidone polymers, and cellulose derivatives.

4. The liquid pharmaceutical composition according to claim 1 wherein said bioadhesive polymer is the copolymer of ethylene and propylene oxide named poloxamer 407.

5. A method for prevention and treatment of gastric hyperacidity and gastroesophageal reflux and related diseases, said method comprising administering a therapeutically effective amount of the pharmaceutical composition according to claim 1, to a subject in need thereof.

6. The method according to claim 5, wherein said pharmaceutical composition is liquid and in the form of unit doses, each consisting of
    a. sodium hyaluronate in an amount of 30 to 100 mg;
    b. sodium chondroitin sulfate in an amount of 80 to 200 mg;
    c. magaldrate in an amount of 400 to 600 mg; and
    d. at least one bioadhesive polymer in a total amount of 100 to 400 mg.

7. A liquid composition in single-dose of 10 ml each, which consists of
    mg/10 ml
    sodium hyaluronate 46.719
    sodium chondroitin sulfate 116.798
    xylitol powder 1262.315
    poloxamer 407 303.000
    polyvinylpyrrolidone 280.517
    sodium benzoate 10.523
    potassium sorbate 21.035
    flavor 2.336
    magaldrate 20% suspension 2500.000
    sucralose 1.685
    xanthan gum 17.969
    water 667.660.

8. The method according to claim 5, wherein said pharmaceutical composition is in single-dose of 10 ml each consisting of
    mg/10 ml
    sodium hyaluronate 46.719
    sodium chondroitin sulfate 116.798
    xylitol powder 1262.315
    poloxamer 407 303.000 polyvinylpyrrolidone 280.517
sodium benzoate 10.523
potassium sorbate 21.035
flavor 2.336
magaldrate 20% suspension 2500.000
sucralose 1.685
xanthan gum 17.969
water 667.660.

9. The pharmaceutical composition according to claim 1, wherein the viscosity is 6,000-7,000 centipoises.

10. The pharmaceutical composition according to claim 1, wherein the pH is 7.9 to 8.4.

11. The pharmaceutical composition according to claim 1, wherein hyaluronic acid or a pharmaceutically acceptable salt thereof has an average molecular weight not lower than $10^5$ Da.

* * * * *